(12) United States Patent
Oberndörfer et al.

(10) Patent No.: US 9,732,833 B2
(45) Date of Patent: Aug. 15, 2017

(54) ELECTROMOTIVE LINEAR DRIVE IN THE FORM OF A DUAL DRIVE

(71) Applicant: DewertOkin GmbH, Kirchlengern (DE)

(72) Inventors: Andreas Oberndörfer, Bielefeld (DE); Jürgen Martin, Bünde (DE)

(73) Assignee: DewertOkin GmbH, Kirchlengern (DE)

( * ) Notice: Subject to any disclaimer, the term of this patent is extended or adjusted under 35 U.S.C. 154(b) by 314 days.

(21) Appl. No.: 14/412,293

(22) PCT Filed: Jun. 27, 2013

(86) PCT No.: PCT/EP2013/063466
§ 371 (c)(1),
(2) Date: Dec. 31, 2014

(87) PCT Pub. No.: WO2014/005912
PCT Pub. Date: Jan. 9, 2014

(65) Prior Publication Data
US 2015/0354679 A1   Dec. 10, 2015

(30) Foreign Application Priority Data
Jul. 3, 2012 (DE) .......... 10 2012 211 514

(51) Int. Cl.
*F16H 25/24* (2006.01)
*F16H 25/20* (2006.01)
*F16H 57/021* (2012.01)

(52) U.S. Cl.
CPC ............ *F16H 25/24* (2013.01); *F16H 25/20* (2013.01); *F16H 57/021* (2013.01);
(Continued)

(58) Field of Classification Search
CPC .. F16H 25/24; F16H 25/20; F16H 2025/2059; F16H 2025/209; F16H 2025/2436
See application file for complete search history.

(56) References Cited

U.S. PATENT DOCUMENTS 3,720,116 A * 3/1973 Better ................. F16H 25/2209
74/409
4,137,946 A * 2/1979 Hardcastle ............... F16J 15/18
138/103

(Continued)

FOREIGN PATENT DOCUMENTS

| | | |
|---|---|---|
| EP | 1900309 A1 | 3/2008 |
| EP | 2080452 A1 | 7/2009 |
| WO | 2013068329 A1 | 5/2013 |

OTHER PUBLICATIONS

Int'l Search Report issued Oct. 8, 2013 in Int'l Application No. PCT/EP2013/063466.

(Continued)

*Primary Examiner* — David M Fenstermacher
(74) *Attorney, Agent, or Firm* — Panitch Schwarze Belisario & Nadel LLP

(57) ABSTRACT

An electromotive linear drive in the form of a dual drive adjust movably mounted parts of reclining and seating furniture. Two threaded spindles (2, 3) driven by a worm gear and which are arranged one behind the other and flush with one another for displacing a lifting element. Bearings are provided at both ends of each threaded spindle (2, 3). The bearings are designed as roller bearings (4, 5) having an inner ring (6) and an outer ring (7). The aim of the invention is to design an electromotive dual drive in such a way that a short overall length is achieved and that the stability of the structure is increased. Said aim is achieved by arranging an abutment between both roller bearings (4, 5), which accom- (Continued)

modate the spindle ends, on which the roller bearings are supported on from both sides.

14 Claims, 1 Drawing Sheet

(52) U.S. Cl.
CPC .................. *F16H 2025/209* (2013.01); *F16H 2025/2059* (2013.01); *F16H 2025/2436* (2013.01); *F16H 2057/0216* (2013.01); *Y10T 74/18576* (2015.01)

(56) References Cited

U.S. PATENT DOCUMENTS

| | | | | |
|---|---|---|---|---|
| 5,199,169 A * | 4/1993 | Bonzak | ................... | B23Q 3/086 29/458 |
| 5,501,118 A * | 3/1996 | Benton | ............... | F16H 25/2209 470/2 |
| 5,868,032 A * | 2/1999 | Laskey | ..................... | F16F 9/58 188/322.12 |
| 5,937,699 A * | 8/1999 | Garrec | ................... | B25J 18/025 74/89.35 |
| 6,101,889 A * | 8/2000 | Laskey | ............... | F16H 25/2204 116/282 |
| 2002/0006846 A1* | 1/2002 | Gallo | .................... | E05F 11/405 475/333 |
| 2005/0115342 A1* | 6/2005 | Barringer | ................ | F16H 25/24 74/89.23 |
| 2005/0179296 A1* | 8/2005 | Bruck | .................... | B60N 2/233 297/361.1 |

OTHER PUBLICATIONS

Int'l Preliminary Report on Patentability issued Jan. 15, 2015 in Int'l Application No. PCT/EP2013/063466.

* cited by examiner

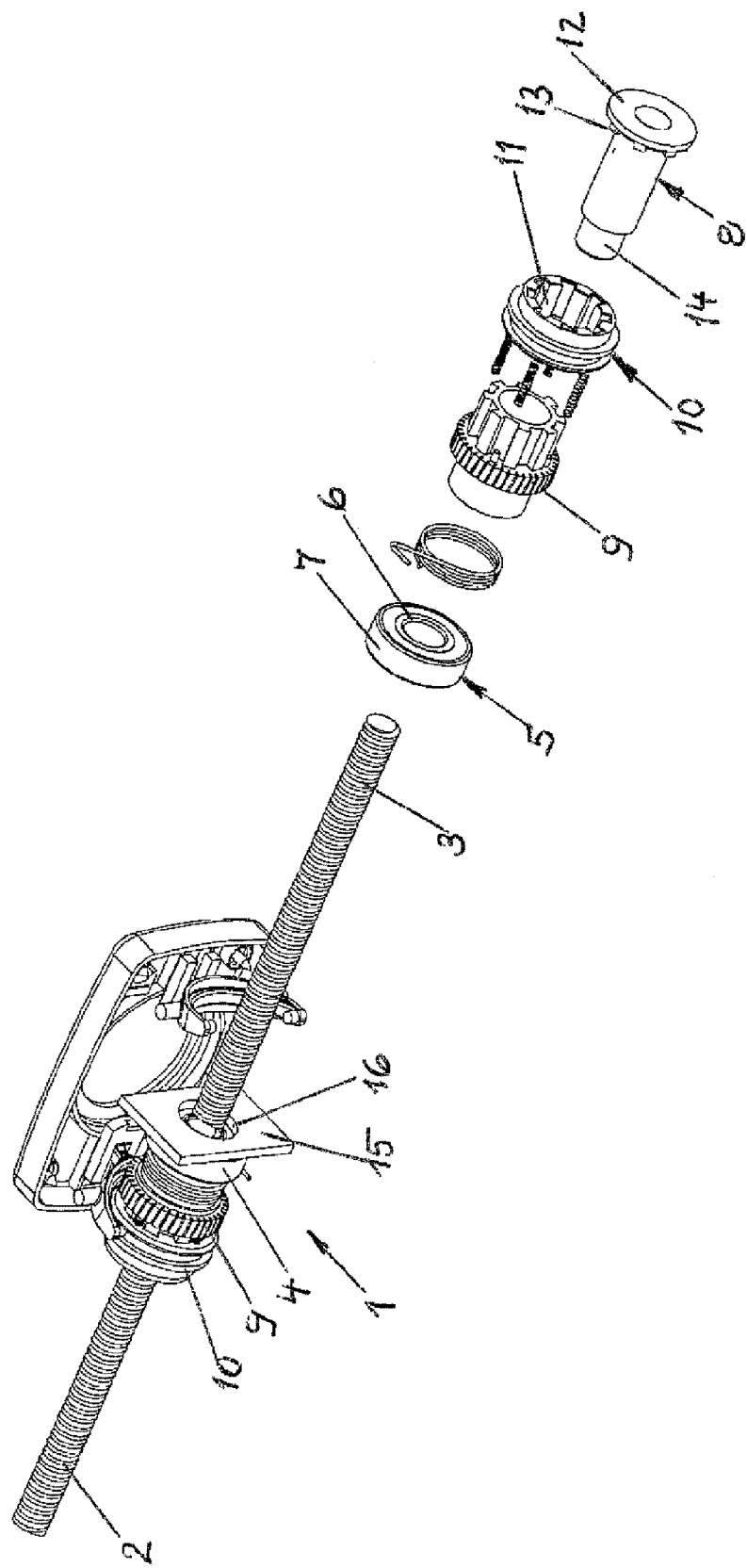

ELECTROMOTIVE LINEAR DRIVE IN THE FORM OF A DUAL DRIVE

CROSS-REFERENCE TO RELATED APPLICATIONS

This application is a Section 371 of International Application No. PCT/EP2013/063466, filed Jun. 27, 2013, which was published in the German language on Jan. 9, 2014, under International Publication No. WO 2014/005912 A1 and the disclosure of which is incorporated herein by reference.

BACKGROUND OF THE INVENTION

The invention concerns an electric motor-actuated linear drive in the form of a dual drive for adjusting moveably mounted parts of lying and seating furniture, in particular for the hospital and care sector, comprising two threaded spindles drivable by way of a respective worm gear transmission and arranged in successive and mutually aligned relationship for displacement of a respective stroke element and bearings provided at both ends of each threaded spindle, wherein at least the bearings arranged at the spindle ends which are close to each other are in the form of rolling bearings having an inner race and an outer race.

Known electric motor-actuated linear drives are generally surrounded by plastic housings in which the individual parts of the respective linear drive are fixed between projecting ribs of the housing which are formed thereon. That is problematical in particular in relation to dual drives which as a result frequently have to be of a great structural length by virtue of the large number of ribs which are of a stable nature.

BRIEF SUMMARY OF THE INVENTION

Therefore the object of the invention is to design an electric motor-actuated dual drive in such a way that a short structural length is achieved and in addition the strength and stability of the structure is increased.

According to the invention that object is attained in that arranged between the two rolling bearings which carry the spindle ends that are close to each other is a support means at which the rolling bearings are mutually supported from both sides.

In the structure according to the invention the counteracting force of the threaded spindles therefore does not have to be carried by the plastic housing, but the two mutually facing ends of the threaded spindles, which ends are carried in rolling bearings, are supported by way of the rolling bearings against the support means provided between them. By virtue of the provision of the support means the structural length of the linear drive can be minimised while at the same time the force contact area between the individual parts is increased and thus the pressure in relation to surface area is minimised.

The support means can be designed in different ways, adapted to the space circumstances and geometrical shapes of the plastic housing surrounding the linear drive. A simple and highly desirable configuration for the support means provides that the support means is in the form of a plate.

Desirably the plate is of a diameter larger than the outside diameter of the outer race of the rolling bearings. That ensures that the entire peripheral region of the outer race of the rolling bearing is supported by the plate.

Preferably the plate has a central round opening whose diameter is smaller than the inside diameter of the outer race of the rolling bearings. In that case the central opening of the plate does not reduce the contact surface area of the outer race but in addition ensures that the outer race bears reliably against the plate, even if possible inner parts like the inner race of the rolling bearing, the end of the guide body or the spindle end project axially beyond the plane of the outer race.

To avoid collisions with possibly projecting parts of the inner race, the guide body or the spindle end the diameter of the central round opening of the plate should be greater than the outside diameter of the inner race of the rolling bearing.

The support means or plate disposed between the bearings can comprise metal, for example steel. The support means can also comprise a zinc or aluminium alloy. That is particularly advantageous when the support means is of a more complicated configuration adapted to the interior circumstances of the housing as then the support means can be produced for example using a die casting method.

Alternatively it is also possible for the support means to be made from plastic, provided that it is of sufficient strength. To ensure this the support means can comprise high-strength, fibre-reinforced plastic.

In order for the support means in the form the plate to be held in optimum fashion in the plastic housing of the linear drive it is preferably rectangular or also square.

Alternatively the plate can also be designed with rounded corners or can be completely round.

In particular ball bearings serve as the rolling bearings in the structure according to the invention.

BRIEF DESCRIPTION OF THE SEVERAL VIEWS OF THE DRAWINGS

The invention is illustrated by means of an embodiment by way of example in the drawing and is described in detail hereinafter with reference to the drawing.

The single FIGURE shows a perspective view of an electric motor-actuated linear drive in the form of a dual drive, which serves for adjusting moveably mounted parts of lying and seating furniture, in particular for the hospital and care sector. For reasons of clarity of the drawing the housing and the stroke elements at both sides thereof have been omitted.

DETAILED DESCRIPTION OF THE INVENTION

On the left-hand side of the drawing the individual transmission parts are assembled while on the right-hand side the parts are shown as an exploded view.

Essentially the dual drive 1 comprises two successively and mutually alignedly arranged threaded spindles 2 and 3 which are drivable by way of a respective worm gear transmission and which serve for displacement of a respective stroke element (not shown) for adjustment of the moveable furniture parts.

Provided at both ends of each threaded spindle 2 and 3 are corresponding bearings. It will be noted however that the drawing only shows the bearings arranged at the spindle ends which are close to each other, those bearings being in the form of rolling bearings 4 and 5 comprising an inner race 6 and an outer race 7.

Arranged on each of the threaded spindles 2 and 3 is a guide body 8 which is carried non-rotatably and non-slidably on the respective threaded spindle 2 and 3.

Of the two worm gear transmissions for driving the two threaded spindles 2 and 3 the drawing only shows the worm gears 9 mounted rotatably on the respective guide body 8. In addition the arrangement has a coupling element 10 which is axially displaceable but which is arranged non-rotatably relative to the respective worm gear and with which the respective worm gear 9 can be selectively coupled to and uncoupled from the associated guide body 8. The inside profile 11 of the coupling element 10 forms in that case, with a counterpart profile 13 provided on a flange 12 of the guide body 8, a dog coupling which can be selectively coupled and uncoupled by axial displacement of the coupling element 10.

When the parts shown in the exploded view are assembled and the guide body 8 is fixed on the threaded spindle 2 or 3 respectively a stepped end 14 of the guide body 8 engages into the central opening of the inner race 6 in the respective rolling bearing 4 and 5.

Arranged between the two rolling bearings 4 and 5 which carry the spindle ends that are close to each other is a steel plate 15, against which the two rolling bearings 4 and 5 bear from opposite sides. The plate 15 which is of a square configuration in the embodiment illustrated in the drawing is in that case selected to be of such a size that the outer races 7 of the rolling bearings 4 and 5 bear over their entire periphery against the plate 15. Alternatively the plate can also have rounded corners or can be completely round.

The plate 15 has a central round opening 16 which passes through the plate 15. The diameter of the opening 16 is smaller than the inside diameter of the outer race 7 of the rolling bearings 4 and 5. This ensures that the outer races 7 of the rolling bearings 4 and 5 bear around same against the flat sides of the plate 15.

In addition the diameter of the central round opening 16 in the plate 15 is larger than the outside diameter of the inner race 6 of the respective rolling bearing 4 and 5 so that the inner race does not come into contact with the plate 15.

In the structure shown in the drawing the stepped end 14 of the guide body 8 also under some circumstances projects a distance beyond the inner race 6 of the respective rolling bearing 4 or 5 so that in that respect no damaging contact with the plate 15 occurs.

The thickness of the plate 15 can be relatively thin. It is only necessary for the thickness of the plate 15 to be sufficient to prevent the rotating parts of the threaded spindles 2 and 3 and the guide body 8 coming into contact.

The plate 15 can comprise steel or also high-strength plastic, for example fibre-reinforced plastic.

The rolling bearings 4 and 5 are in the form of ball bearings.

By virtue of the structure according to the invention the axial forces exerted on the threaded spindles 2 and 3 upon adjustment of the furniture parts are not transmitted to the housing and possible internal holding ribs, but the threaded spindles 2 and 3 are supported against the plate 15 from both sides by way of the ball bearings.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An electric motor-actuated linear drive for adjusting moveably mounted parts of lying and seating furniture, comprising two threaded spindles (2, 3) drivable by way of a respective worm gear transmission and arranged in successive and mutually aligned relationship for displacement of a respective stroke element and bearings provided at both ends of each threaded spindle (2, 3), wherein at least the bearings arranged at the spindle ends which are close to each other are in the form of rolling bearings (4, 5) having an inner race (6) and an outer race (7), characterised in that arranged between the two rolling bearings (4, 5) which carry the spindle ends that are close to each other is a support means at which the rolling bearings are mutually supported from both sides.

2. An electric motor-actuated linear drive according to claim 1, wherein the support means is in the form of a plate (15).

3. An electric motor-actuated linear drive according to claim 2, wherein the plate (15) is of a diameter larger than the outside diameter of the outer race (7) of the rolling bearings (4, 5).

4. An electric motor-actuated linear drive according to claim 2, wherein the plate (15) has a central round opening (16) whose diameter is smaller than the inside diameter of the outer race (7) of the rolling bearings (4, 5).

5. An electric motor-actuated linear drive according to claim 4, wherein the diameter of the central round opening (16) of the plate (15) is larger than the outside diameter of the inner race (6) of the rolling bearings (4, 5).

6. An electric motor-actuated linear drive according to claim 1, wherein the support means or the plate (15) comprises metal.

7. An electric motor-actuated linear drive according to claim 6, wherein the support means or the plate (15) comprises steel.

8. An electric motor-actuated linear drive according to claim 6, wherein the support means or the plate (15) comprises a zinc or aluminium alloy.

9. An electric motor-actuated linear drive according to claim 1, wherein the support means or the plate (15) comprises plastic.

10. An electric motor-actuated linear drive according to claim 9, wherein the support means or the plate (15) comprises high-strength, fibre-reinforced plastic.

11. An electric motor-actuated linear drive according to claim 2, wherein the plate (15) is rectangular or square.

12. An electric motor-actuated linear drive according to claim 2, wherein the plate has rounded corners.

13. An electric motor-actuated linear drive according to claim 2, wherein the plate is round.

14. An electric motor-actuated linear drive according to claim 1, wherein ball bearings are provided as the rolling bearings (4, 5).

* * * * *